United States Patent [19]
Akiyama

[11] Patent Number: 6,126,287
[45] Date of Patent: Oct. 3, 2000

[54] OPERATION MICROSCOPE

[75] Inventor: Hiroshi Akiyama, Tokyo, Japan

[73] Assignee: Kabushiki Kaisha Topcon, Tokyo, Japan

[21] Appl. No.: 09/349,248

[22] Filed: Jul. 8, 1999

[30] Foreign Application Priority Data

Jul. 13, 1998 [JP] Japan ................................. 10-197194

[51] Int. Cl.⁷ ....................................................... A61B 3/10
[52] U.S. Cl. ............................................................ 351/221
[58] Field of Search .................................... 351/208, 210, 351/211, 212, 213, 214, 219, 221; 359/554, 557; 396/51, 281; 606/4

[56] References Cited

U.S. PATENT DOCUMENTS

| | | | |
|---|---|---|---|
| 4,753,526 | 6/1988 | Koester | 351/219 |
| 5,386,258 | 1/1995 | Nagano | 351/210 |
| 5,555,040 | 9/1996 | Kaneko | 351/221 |
| 5,557,351 | 9/1996 | Kasahara et al. | 351/221 |
| 5,801,807 | 9/1998 | Satake et al. | 351/221 |
| 5,914,771 | 6/1999 | Biber | 351/221 |

*Primary Examiner*—George Manuel
*Attorney, Agent, or Firm*—Armstrong, Westerman, Hattori, McLeland & Naughton

[57] ABSTRACT

A light-shielding member is provided at an optically conjugative position with an optical system composed of optical components (including a corneal convex mirror) interposed between an entrance pupil and the light-shielding member on an optical path of an illumination optical system in order to prevent a virtual image of a light source from being observed in an observation optical system. The position where the light-shielding member is located is the vicinity of an illumination field stop and closer to the eye to be examined than the illumination field stop. A size of the light-shielding member is theoretically determined by a product of a diameter of the entrance pupil of the observation optical system, and an observation magnification of the optical system composed of the corneal convex mirror and a relay lens.

11 Claims, 6 Drawing Sheets

OPERATION MICROSCOPE

BACKGROUND OF THE INVENTION

1. Field of the Invention

The present invention relates to an operation microscope for illuminating and observing eyes to be examined, of a subject such as a patient in diagnosis, medical treatment and operation in ophthalmology.

2. Description of Related Art

An operation microscope is known which illuminates eyes of a subject such as a patient with an illumination optical system and with which an observer can stereoscopically observe the illuminated eyes through a binocular stereoscopic observation optical system in diagnosis, medical treatment and operation in ophthalmology.

Figure 1:
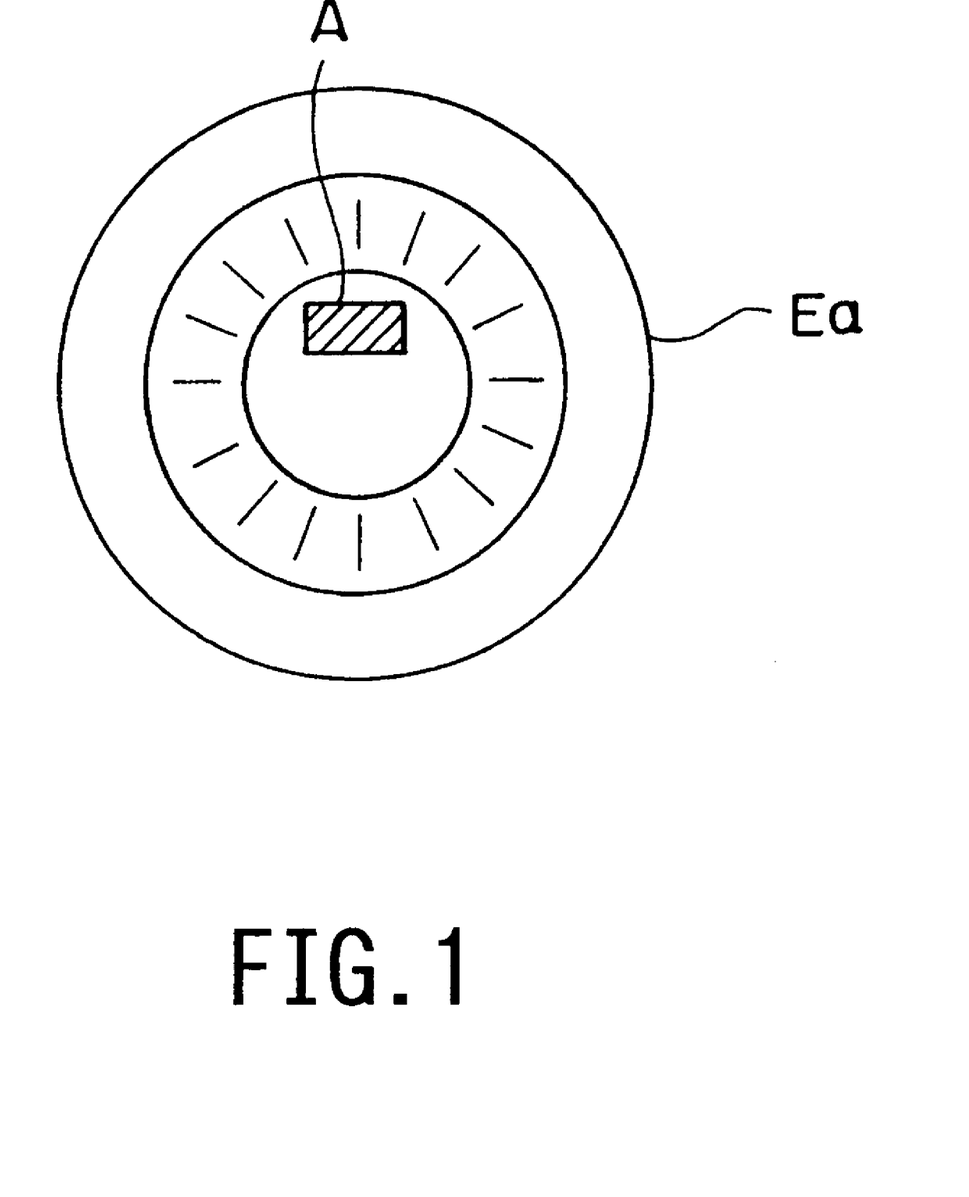
FIG. 1 is a view explaining a virtual image of a light source observed by illumination to an eye to be examined in a conventional operation microscope.

However, in the case where an eye is illuminated with a conventional operation microscope, a cornea of the eye to be examined acts as a convex reflective mirror, so that a virtual image of the illumination light source is formed on the focal surface of the cornea. For this reason, as shown in FIG. 1, the virtual image A of the illumination optical source of the illumination optical system is observed in the observation optical system. Thus, it is a disadvantage that the virtual image A of the illumination light source would obstruct the observation when the observer observes the inherent image Ea of the eye to be examined.

Although the virtual image of the illumination light source observed in the observation optical system is not so large in physical size, this virtual image seems as if the light source was present on the cornea. Accordingly, the virtual image is too bright in comparison with other portions, and then it is difficult to observe the other portions by the observer.

Also, blurs or the like caused by diffused reflection produce in the vicinity of the virtual image of the illumination light source. Accordingly, also in this case, the observer observes the vicinity of the virtual image with difficulty.

Further, since the virtual image of the illumination light source is extremely bright, the virtual image offsets the observation light from a portion deeper from the eye to be examined than the portion where the virtual image is positioned, so that it is difficult to observe the deep portion. Also, the attention of the observer would be always dispersed due to the presence of the virtual image, so that the observer cannot concentrate his or her attention to the observation of other portions.

Furthermore, when the virtual image of the illumination light source is incident into the observation optical system, there is a fear that the internal reflection would occur within the observation optical system. If such internal reflection would occur, a flare or a reduction in contrast of the observation image would be caused, resulting in degradation of the condition of the observation image.

On the other hand, according to an operation microscope disclosed in the publication of Japanese Examined Patent Application No. 7-71551, a light absorbing filter is provided in a plane conjugative with an object surface of a central region of the illumination optical path. Therefore, a central shade equal to a pupil diameter is caused in the cornea of the eye to be examined, and then a retina damage of the eye to be examined may be prevented. In an operation microscope with such a structure, the virtual image of the illumination light source as described above is not observed in the observation optical system. However, since the pupil region is not observed at all in such an operation microscope, it is a disadvantage that this operation microscope could not be used for the operation that needs the observation of the pupil region such as crystal lens extracting operation.

SUMMARY OF THE INVENTION

The present invention has been made in view of the above circumstance, and therefore it is an object of the present invention to provide an operation microscope for clearly observing a crystal lens or the like of an eye to be examined, by effectively removing a virtual image of an illumination light source by corneal reflection of the eye.

In order to solve the above problems, according to the present invention, there is provided an operation microscope, having an illumination optical system for illuminating an eye to be examined by an illumination light flux from a light source and an observation optical system for observing the eye to be examined, wherein a light-shielding member for preventing a virtual image of the light source to be formed on the eye to be examined by the illumination light flux from being observed is provided on an optical path of the illumination optical system at on an optically conjugative position with an entrance pupil of the observation optical system.

According to the operation microscope of the present invention, it is characterized in that a size of the light-shielding member is determined in accordance with an imaging magnification of an optical system formed by optical components existing between the light-shielding member and the entrance pupil, and by a cornea of the eye to be examined.

According to the operation microscope of the present invention, it is characterized in that the size of the light-shielding member is determined in accordance with the optical components and aberration of the cornea of the eye to be examined.

According to the operation microscope of the present invention, it is characterized in that the size of the light-shielding member is determined in view of movement of the eye to be examined during the operation.

Also, in order to solve the above problems, according to the present invention, there is provided an operation microscope, having an illumination optical system for illuminating an eye to be examined by an illumination light flux from a light source and an observation optical system for observing the eye to be examined, wherein a light-shielding member for preventing a virtual image of the light source to be formed on the eye to be examined by the illumination light flux from being observed is provided at a position of an illumination field stop for determining the size of an illumination field of the illumination optical system.

According to the operation microscope of the present invention, it is characterized in that the observation optical system has a variable optical system for changing an observation magnification, and the light-shielding member is located at an optically conjugative position with a position of the entrance pupil in the case where the observation optical system is set at a predetermined observation magnification by the variable optical system.

DETAILED DESCRIPTION OF THE PREFERRED EMBODIMENTS

An embodiment of the present invention will now be described with reference to the accompanying drawings.

[Principle of the Invention]

Figure 2:
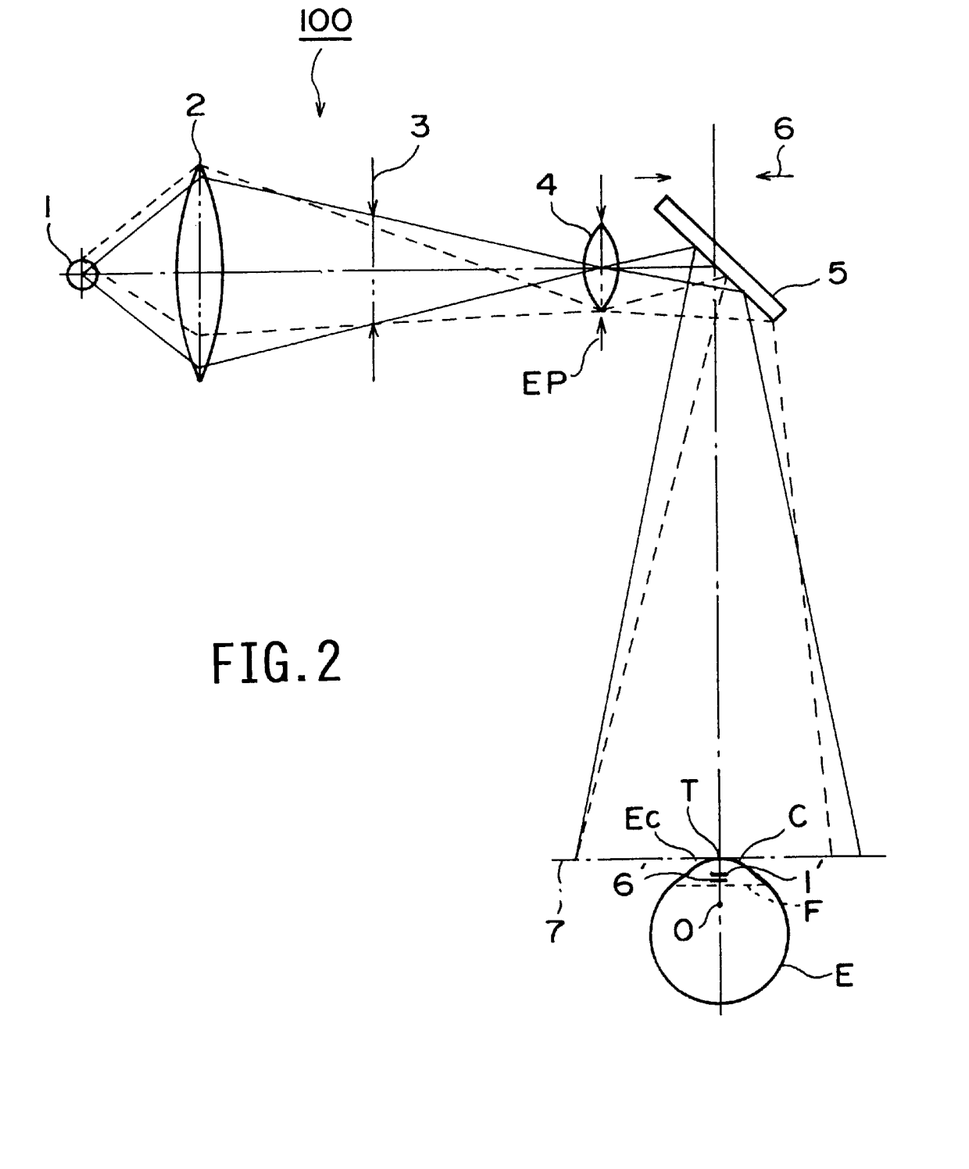
FIG. 2 shows the structure of the conventional operation microscope.
Figure 3:
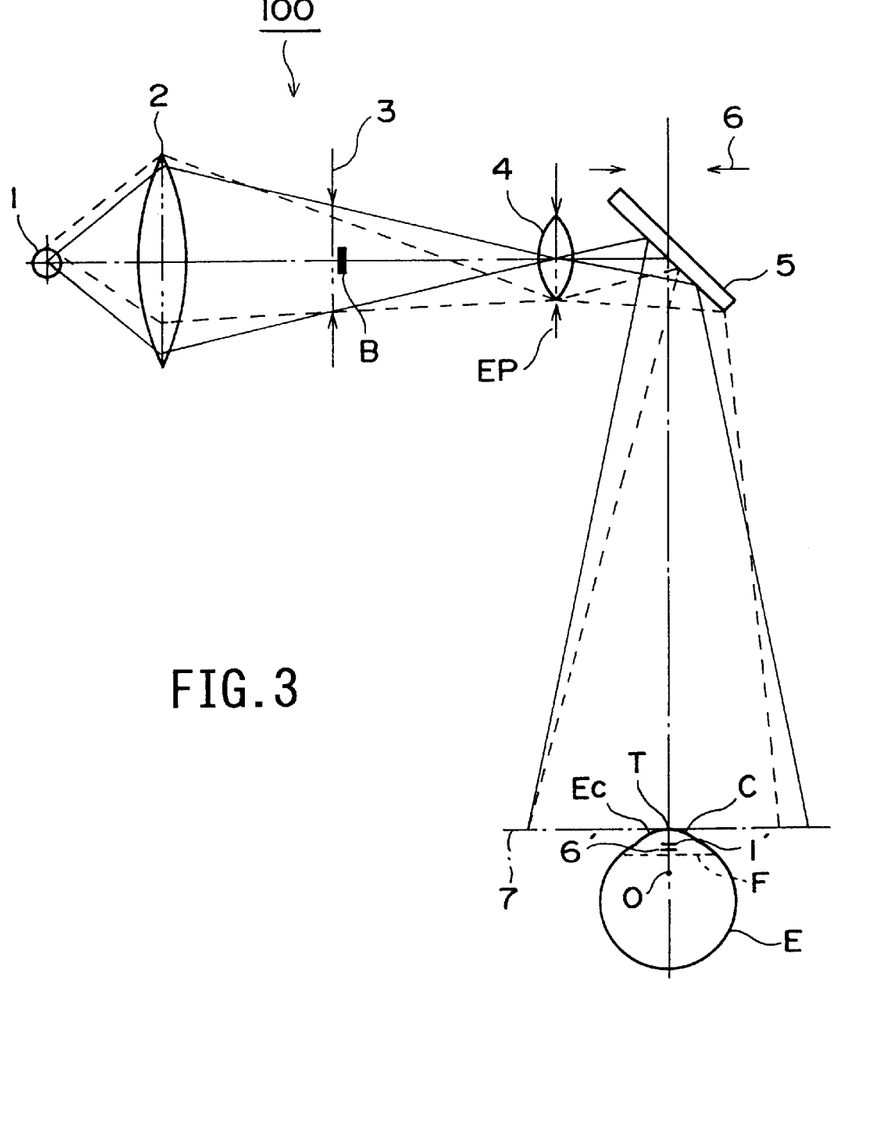
FIG. 3 shows the structure of an operation microscope in accordance with an embodiment of the present invention.

The principle of the present invention will be first described on the basis of FIGS. 2 and 3.

FIG. 2 shows the structure of the conventional operation microscope and FIG. 3 shows the structure of an operation microscope according to the embodiment of the present invention.

As shown in FIG. 2, the conventional operation microscope has an illumination optical system 100 for illuminating an eye E to be examined. Incidentally, since the observation optical system is not directly related to the present invention, only an entrance pupil 6 of the observation optical system (hereinafter simply referred to as an entrance pupil 6) is shown.

As shown in FIG. 2, the illumination optical system 100 has a light source 1, a condenser lens 2, an illumination field stop 3, a relay lens 4, and a half-mirror 5.

The illumination light emitted from the light source 1 is converged at the condenser lens 2 and illuminated on the illumination field stop 3. The illumination field stop 3 is a stop for determining a size of an illumination field on an object surface 7. An illumination light flux passed through the illumination field stop 3 forms an image of the light source 1 once at a position of the relay lens 4. Namely, this operation microscope is constructed so that an exit pupil EP of the illumination optical system 100 corresponds to the position of the relay lens 4.

The illumination light flux from the exit pupil EP is reflected in a direction toward the eye E to be examined by the half-mirror 5, to illuminate the eye E to be examined. Since the illumination field stop 3 is conjugative with the object surface 7 with respect to the relay lens 4, the eye E to be examined, located on the object surface 7 is illuminated in the form of the illumination field stop 3. Incidentally, it is assumed that the object surface 7 corresponds to a corneal apex T of the eye E to be examined.

A portion of the light flux for illuminating the eye E to be examined is thus reflected at a cornea C so that, in the case where the cornea C is regarded as the convex mirror, a virtual image 1' (a virtual image of the light source 1) of the exit pupil EP is formed in the vicinity of a focal plane F of the convex mirror (hereinafter referred to as a cornea convex mirror Ec). Then, since the portion of this virtual image forming light flux reaches the entrance pupil 6 through the half-mirror 5, the virtual image 1' of the exit pupil EP, i.e., the virtual image of the light source 1 is observed in the observation optical system. This becomes a hindrance in the observation of the eye E to be examined.

Therefore, as shown in FIG. 3, in the operation microscope in accordance with the embodiment of the present invention, in order to prevent the virtual image of the light source 1 from being observed in the observation optical system, a light-shielding member B is provided in an optical path of the illumination optical system 100. The light-shielding member B is provided at a position which is optically conjugative with the entrance pupil 6 with respect to the optical system formed by optical members (including the corneal convex mirror Ec) interposed between the entrance pupil 6 and the light-shielding member B. In case of FIG. 3, the light-shielding member B is disposed at an optically conjugative position with the entrance pupil 6 with respect to the optical system composed of the corneal convex mirror Ec and the relay lens 4.

The position where the light-shielding member B is disposed is in the vicinity of the illumination field stop 3 and closer to the eye E to be examined than the illumination field stop 3. The reason for this is as follows.

Namely, a distance between the entrance pupil 6 and the corneal convex mirror Ec is regularly about 200 mm and is long enough in comparison with the focal distance (about 3.8 mm) of the corneal convex mirror Ec. For this reason, the virtual image 6' of the entrance pupil 6 by the corneal convex mirror Ec is formed in the vicinity of the focal plane F of the corneal convex mirror Ec. Thus, the position of the virtual image 6' of the entrance pupil 6 is different from that of the object surface 7 where a real image of the illumination field stop 3 is formed only by about 3 mm.

Accordingly, the position, in the optical path of the illumination optical system 100, which is optically conjugative with the virtual image 6' of the entrance pupil 6 with respect to the relay lens 4 is in the vicinity of the illumination field stop 3 and closer to eye E to be examined than the illumination field stop 3.

As a result, The optically conjugative position with the entrance pupil 6 with respect to the optical system composed of the corneal convex mirror Ec and the relay lens 4 is in the vicinity of the illumination field stop 3 and is closer to the eye E to be examined than the illumination field stop 3. In the aforementioned microscope, the position is shifted by about 1 mm in the direction toward the eye E to be examined from the illumination field stop 3, though differing depending on the form of the illumination optical system 100. Accordingly, by locating the light-shielding member B at this position, the virtual image of the light source 1 is prevented from being observed in the observation optical system.

Subsequently, a size of the light-shielding member B is determined by an observation magnification M of the optical system composed of the corneal convex mirror Ec and the relay lens 4. In other words, the product of a diameter of the entrance pupil 6 of the observation optical system and the observation magnification M makes the size of the light-shielding member B that is theoretically needed.

Here, the imaging magnification M of the optical system composed of the corneal convex mirror Ec and the relay lens 4 is represented as follows.

$$M = fc/b^{(f+a)}$$

where a is the distance between the entrance pupil 6 and the corneal convex mirror Ec, f is the focal distance of the corneal convex mirror Ec, b is the distance between the corneal convex mirror Ec and the relay lens 4, and c is the distance between the relay lens 4 and the illumination field stop 3.

For instance, in the case where a=200 (mm), f=3.8 (mm), b=200 (mm), and c=70 (mm), in accordance with the above equation, the imaging magnification, M=0.0065, is obtained. Accordingly, in the case that the diameter of the entrance pupil 6 is 15 (mm), the diameter of the light-shielding member B which is theoretically needed is represented as follows: 15 (mm)×0.0065=0.098 (mm).

In this connection, according to the operation microscope described in the publication of Japanese Patent Examined Publication No. 7-71551, the size of the light-shielding member for generating a central shade equal to the pupil diameter to prevent a retina damage of the patient is in the range of about 2 to 4 mm in view of the size of the pupil diameter and the magnification of the relay lens 4, and is considerably different from the size of the light-shielding member B according to the present invention.

The position and the size of the above described light-shielding member B are an ideal position and an ideal size. Accordingly, as far as the purpose of clear observation of the crystal lens or the like of the eye E to be examined with an effective removal of the virtual image of the light source 1 caused by the corneal reflection of the eye E to be examined is attained, it is possible to locate the light-shielding member B at a position shifted by a minute distance from the above described ideal position, or to use the light-shielding member B that is larger in size than the size to be needed by several % or more.

For example, in view of the aberration of the optical system or the movement of the eye E to be examined during the operation, it is also possible to provide the light-shielding member having a size which is about five to ten times (0.5 to 1.0 mm in this case) greater than that of the above described ideal value.

Also, theoretically, the ideal position of the light-shielding member B is apart by about 1 mm from the position of the illumination field stop 3. However, actually, although the position of the light-shielding member B corresponds to the position of the illumination field stop 3, the purpose of clear observation of the crystal lens or the like of the eye E to be examined with an effective removal of the virtual image of the light source 1 caused by the corneal reflection of the eye E to be examined is attained sufficiently.

Namely, if the light-shielding member B is located at the position of the illumination field stop 3, there is a disadvantage that the image of the light-shielding member B is formed on the object surface 7. However, the size of the light-shielding member B is about 1.0 mm large at best and very small. Thus, the size of the image of the light-shielding member B is about 3.0 mm at maximum. In addition, the image of the light-shielding member B is removed, by the diffused reflection light from the eye bottom or the iris of the eye E to be examined, to such an extent that the observer does not pay any attention to the image. Accordingly, this will not cause a serious hindrance in the observation of the eye E to be examined. Rather, since it is possible to integrally form the illumination field stop 3 and the light-shielding member B with each other, the number of the components can be reduced, and then the manufacturing cost can be lowered advantageously. Thus, it is sufficient to design the optical system, taking into consideration the merits and demerits in comparison.

Also, in case of the operation microscope, since the observation optical system is usually provided so that the image may be actually observed by both the right and left eyes, the entrance pupil 6 of the observation optical system exists in each of a pair of optical systems for the right and left eyes. Accordingly, also, the light-shielding member B has to be provided to correspond each of the images of the pair of entrance pupils 6.

A specific structure of the operation microscope utilizing the above principle of the present invention will be described.

Figure 4:
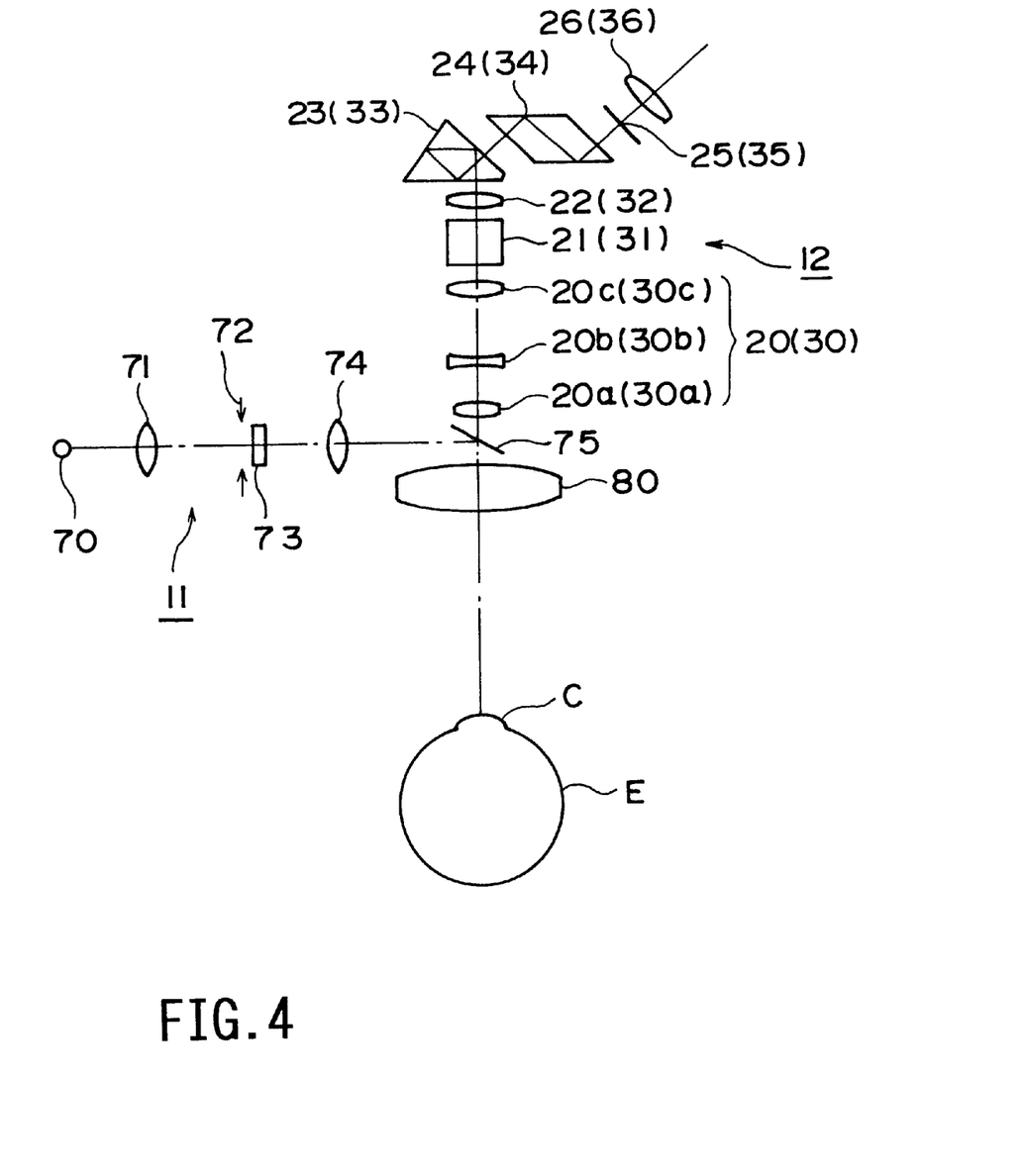
FIG. 4 shows an illumination optical system and an observation optical system of the operation microscope in accordance with the embodiment of the present invention.
Figure 5:
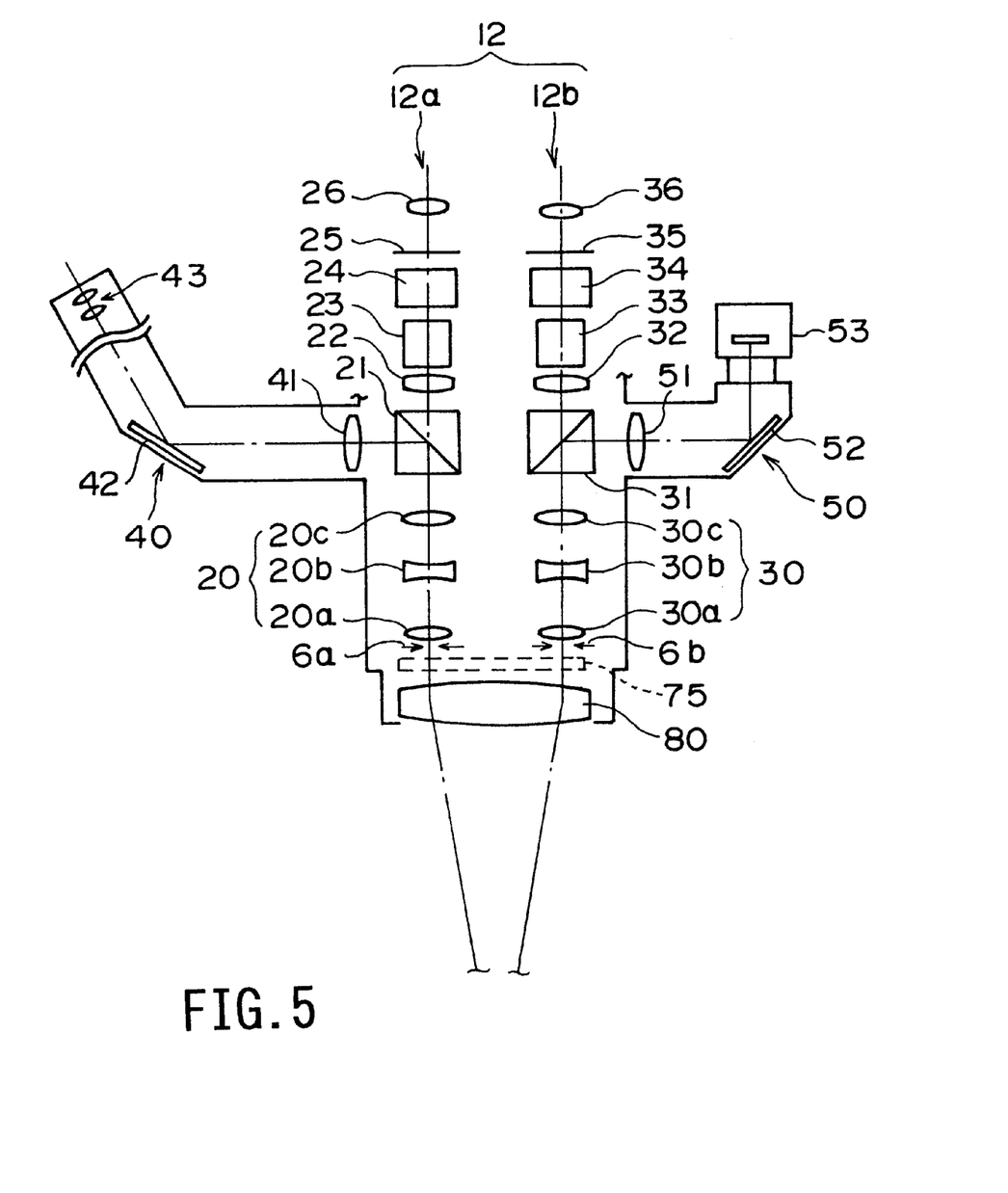
FIG. 5 shows the illumination optical system and the observation optical system of the operation microscope in accordance with the embodiment of the present invention.
Figure 6A:
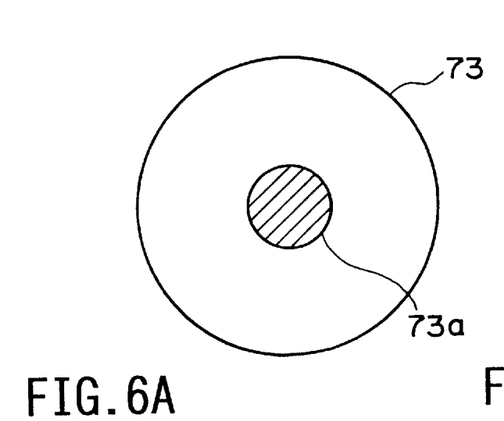
FIGS. 6A to 6F show examples of light-shielding members having light-shielding portions with predetermined sizes and shapes disposed on optical paths of the illumination optical system of the operation microscope in accordance with the embodiment of the present invention.
Figure 6B:
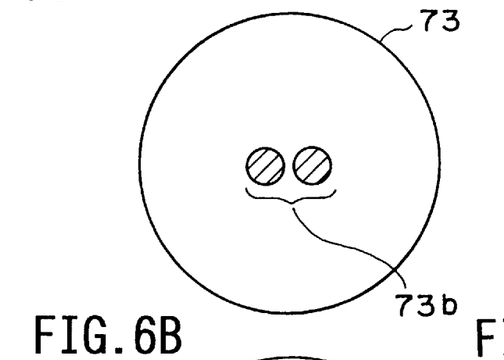
Figure 6C:
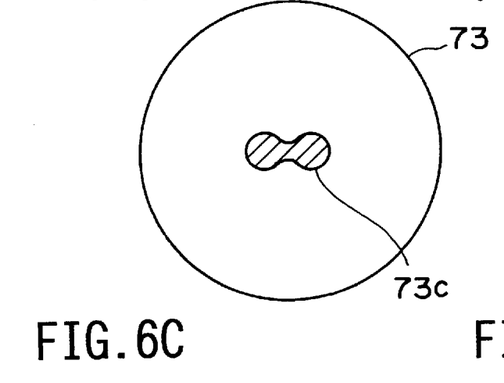
Figure 6D:
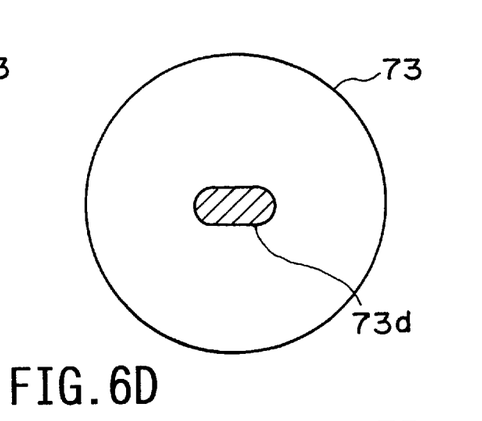
Figure 6E:
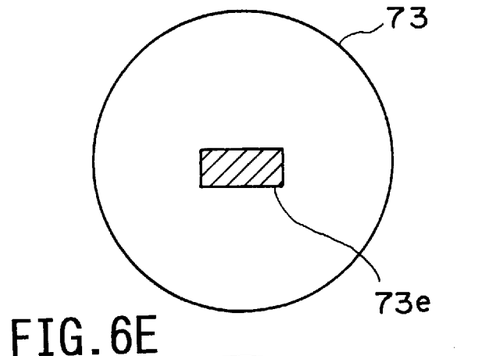
Figure 6F:
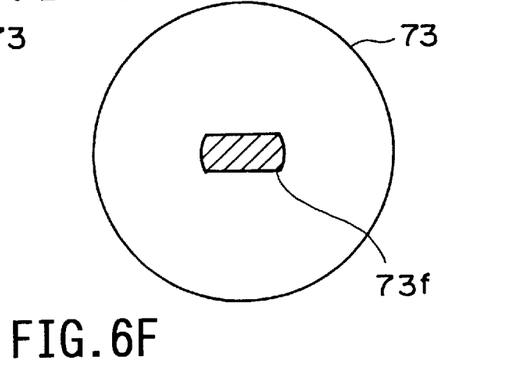

FIGS. 4 and 5 show the structure of the operation microscope in accordance with an embodiment of the present invention. In FIGS. 4 and 5, the operation microscope in accordance with the embodiment of the present invention has an illumination optical system 11 and an observation optical system 12.

The illumination optical system 11 is constructed by a light source 70 composed of a halogen lamp or the like, a condenser lens 71, an illumination field stop 72, a light-shielding member 73, a relay lens 74, a half mirror 75 and an objective lens 80.

The illumination light emitted from the light source 70 passes through the condenser lens 71, the illumination field stop 72, the light-shielding member 73, and the relay lens 74, and is reflected by the half mirror 75 to be projected through the objective lens 80 onto the eye E to be examined.

The observation optical system 12 has a right eye observation optical system 12*a* and a left eye observation optical system 12*b*. The right eye observation optical system 12*a* is constructed by the objective lens 80, a variable optical system 20 composed of variable lenses having three lenses 20*a*, 20*b* and 20*c*, a beam splitter 21, an imaging lens 22, prisms 23 and 24, a field stop 25, and an eyepiece 26.

Also, in the same manner as in the right eye observation optical system 12*a*, the left eye observation optical system 12*b* is constructed by the objective lens 80, a variable optical system 30 composed of variable lenses having three lenses 30*a*, 30*b* and 30*c*, a beam splitter 31, an imaging lens 32, prisms 33 and 34, a field stop 35, and an eyepiece 36.

The light illuminated on the eye E to be examined by the illumination optical system 11 is reflected at the eye E to be examined. The reflected light is observed by both right and left eyes of the observer through the objective lens 80, the half mirrors 75, the variable optical systems 20 and 30, the beam splitters 21 and 31, the imaging lenses 22 and 32, the prisms 23, 24, 33, and 34, the field stops 25 and 35, and the eyepieces 26 and 36.

Also, the reflected light from the eye E to be examined is split by the beam splitters 21 and 31. The light split by the beam splitter 21 is introduced into an auxiliary observation optical system 40 composed of an imaging lens 41, a reflective mirror 42, and an eyepiece 43, and may be observed by another observer.

The light split by the beam splitter 31 is introduced into a television imaging optical system 50 composed of an imaging lens 51, a reflective mirror 52, and a television camera 53, and thus television imaging can be performed.

Incidentally, in the right eye observation optical system 12*a* and the left eye observation optical system 12*b* of the observation optical system 12, the entrance pupils 6*a* and 6*b* exist, respectively.

The light-shielding member 73 for shielding only the corneal reflective light which is introduced into the entrance pupils 6*a* and 6*b* of the observation optical system 12 and which forms the virtual image of the light source 70 will now be described.

The light-shielding member 73 is composed of a planar glass or the like, and is provided insertably into the optical path of the illumination optical system 11. Furthermore, the light-shielding member 73 is disposed on the optical path of the illumination optical system 11 and at an optically conjugative position with the entrance pupils 6*a* and 6*b* of the observation optical system 12 with respect to the optical system composed of the corneal convex mirror Ec, the objective lens 80 and the relay lens 74. Incidentally, in the case where the observer does not pay the attention about the existence of the virtual image of the light source 70 to be observed in the observation optical system 12 during the observation of the eye E to be examined, it is possible to remove the light-shielding member 73 from the optical path of the illumination optical system 11.

As described above, the entrance pupils 6a and 6b exist, respectively, for the right eye observation optical system 12a and the left eye observation optical system 12b of the observation optical system 12 of the binocular operation microscope. Accordingly, it is desirable that the light-shielding portion provided in the light-shielding member 73 is formed to have a size and a shape so as to cover the overall entrance pupils 6a and 6b of the right eye observation optical system 12a and the left eye observation optical system 12b.

For example, as shown in FIGS. 6A to 6F, it is possible to provide a circular shape 73a, a double circular shape 73b, a substantially circular-combined shape 73c, an oblong shape 73d, a rectangular shape 73e and an substantially rectangular shape 73f, respectively, in the light-shielding member 73. Also, for example, the light-shielding portion provided in the light-shielding member 73 can be formed into an ellipse shape.

Namely, the light-shielding portion provided in the light-shielding member 73 has a size and a shape so as not to shield all the light flux emitted from the light source 70, it has a size and a shape that are needed to shield only the light flux forming the virtual image of the light source 70 introduced into the respective entrance pupils 6a and 6b of the right eye observation optical system 12a and the left eye observation optical system 12b of the observation optical system, in the cornea reflective light by the surface reflection of the cornea C of the eye E to be examined.

Incidentally, as described above, the size and the shape of the light-shielding portion provided in the light-shielding member 73 are determined on the basis of the sizes, the shapes and the positions of the entrance pupils 6a and 6b of the observation optical system 12, and the observation magnification by the variable optical systems 20 and 30 of the observation optical system 12 composed of the optical components interposed between the cornea C of the eye E to be examined and the optically conjugative position with the entrance pupils 6a and 6b.

For instance, in the case where the observation optical system 12 has the variable optical systems 20 and 30 as in the operation microscope in accordance with the embodiment of the present invention, the sizes and the positions of the entrance pupils 6a and 6b of the observation optical system 12 are changed in accordance with the movement of the variable optical systems 20 and 30 along the optical axes thereof. As a result, the optically conjugative position with the entrance pupils 6a and 6b of the observation optical system 12 on the optical path of the illumination optical system 11 is changed (moved).

Thus, in the case where the observation magnification of the observation optical system 12 is changed by the variable optical systems 20 and 30, the positions and the sizes of the entrance pupils 6a and 6b of the observation optical system 12 are also changed. Accordingly, it is desirable to change the position and the size of the light-shielding portions provided in the light-shielding member 73 on the optical path of the illumination optical system 11 in accordance with the change in observation magnification of the observation optical system 12.

Incidentally, the degree of change in positions and sizes of the entrance pupils 6a and 6b of the observation optical system 12 on the basis of the change in observation magnification of the observation optical system 12 by the variable optical systems 20 and 30 are extremely small. Accordingly, in the case where the observation optical system 12 is set at a predetermined observation magnification by the variable optical systems 20 and 30, if the light-shielding member 73 having the light-shielding portion with a predetermined size is located at a predetermined conjugative position on the optical path of the illumination optical system 11 with the entrance pupils 6a and 6b of the observation optical system 12, it is unnecessary to move the light-shielding member 73 in response to the observation magnification of the observation optical system 12.

For example, according to the operation microscope in which the observation magnification of the observation optical system 12 can be changed within the range from five times to twenty times by the variable optical systems 20 and 30, the light-shielding member 73 is located and fixed at the predetermined conjugative position on the optical path of the illumination optical system 11 with the position of the entrance pupils 6a and 6b in case where the observation magnification of the observation optical system 12 is set at ten times.

Also, it is preferable that the size of the light-shielding portion provided in the light-shielding member 73 is set in conformity with the observation magnification at which the size of the entrance pupils 6a and 6b of the observation optical system 12 is at maximum.

As described above, according to the operation microscope in accordance with the present invention, the light-shielding member is disposed at a conjugative position with the entrance pupils of the observation optical system on the optical path of the illumination optical system, so that the crystal lens or the like of the eye to be examined can be clearly observed while effectively removing the virtual image of the light source caused by the corneal reflection of the eye to be examined. Thus, the diagnosis, treatment and operation in ophthalmology may be performed in a smooth and exact manner, so that any load to be imposed on the patient, the observer et al. can be considerably suppressed.

What is claimed is:

1. An operation microscope, comprising:
   an illumination optical system for illuminating an eye to be examined with a light source;
   an observation optical system for observing the eye; and
   a light-shielding member disposed in the optical path of said illumination optical system in order to prevent the virtual image of the light source to be formed on the eye from being observed,
   said light shielding member being disposed at a position optically conjugate with the entrance pupil of the observation optical system.

2. The operation microscope according to claim 1, wherein a size of the light-shielding member is determined in accordance with an imaging magnification of an optical system formed by optical components existing between the light-shielding member and the entrance pupil, and by a cornea of the eye to be examined.

3. The operation microscope according to claim 2, wherein the size of the light-shielding member is determined in accordance with the optical components and aberration of the cornea of the eye to be examined.

4. The operation microscope according to claim 3, wherein the size of the light-shielding member is determined in view of movement of the eye to be examined during the operation.

5. The operation microscope according to claim 2, wherein the size of the light-shielding member is determined in view of movement of the eye to be examined during the operation.

6. The operation microscope according to claim 1, wherein the observation optical system has a variable optical system for changing an observation magnification, and the light-shielding member is located at an optically conjugative position with a position of the entrance pupil in the case where the observation optical system is set at a predetermined observation magnification by the variable optical system.

7. An operation microscope, comprising:

an illumination optical system for illuminating an eye to be examined with a light source;

an observation optical system for observing the eye;

an illumination field stop for determining the size of an illumination field of the illumination optical system; and a light-shielding member disposed in the optical path of said illumination optical system in order to prevent a virtual image of the light source to be formed on the eye from being observed, said light shielding member being disposed at a position of said illumination field stop.

8. The operation microscope according to claim 7, wherein a size of the light-shielding member is determined in accordance with an imaging magnification of an optical system formed by optical components existing between the light-shielding member and the entrance pupil and by a cornea of the eye to be examined.

9. The operation microscope according to claim 8, wherein the size of the light-shielding member is determined in accordance with the optical components and aberration of the cornea of the eye to be examined.

10. The operation microscope according to claim 9, wherein the size of the light-shielding member is determined in view of movement of the eye to be examined during the operation.

11. The operation microscope according to claim 8, wherein the size of the light-shielding member is determined in view of movement of the eye to be examined during the operation.

* * * * *